United States Patent [19]

Dieffenbach

[11] Patent Number: 5,089,421
[45] Date of Patent: Feb. 18, 1992

[54] METHOD AND APPARATUS FOR ANALYZING BLOOD

[76] Inventor: Susan Dieffenbach, 6082 Irongate Cir., Huntington Beach, Calif. 92648

[21] Appl. No.: 502,251

[22] Filed: Mar. 30, 1990

Related U.S. Application Data

[63] Continuation-in-part of Ser. No. 307,227, Feb. 6, 1989, abandoned, which is a continuation of Ser. No. 110,972, Oct. 20, 1987, abandoned.

[51] Int. Cl.⁵ .................. G01N 33/48; G01N 33/50
[52] U.S. Cl. ............................. 436/68; 436/63; 128/632; 128/635
[58] Field of Search .................. 436/68, 63; 128/632-635, 765

[56] References Cited

U.S. PATENT DOCUMENTS

| | | | |
|---|---|---|---|
| 3,469,199 | 3/1972 | Littlejohn | 128/2 R |
| 4,466,878 | 8/1984 | DiNitto et al. | 204/415 |
| 4,467,811 | 8/1984 | Clark | 128/635 |
| 4,512,349 | 4/1985 | Hunt et al. | 128/632 |
| 4,608,996 | 9/1986 | Brown | 128/760 |

*Primary Examiner*—Robert J. Hill, Jr.
*Assistant Examiner*—David Redding
*Attorney, Agent, or Firm*—Nydegger & Associates

[57] ABSTRACT

An apparatus for analyzing blood comprises a conduit formed with a passageway. The conduit is also formed with an inlet, an outlet and an aperture, each of which are in fluid communication with the passageway. An adapter is threadably engageable with the conduit to hold a membrane therebetween over the aperture. A syringe is engageable with the outlet to draw blood into the passageway through the inlet and into contact with the membrane. The electrode of a blood gas analyzer is engageable with the adapter to position the electrode against the side of the membrane opposite the side in contact with the blood for analyzing the oxygen status of the blood.

6 Claims, 1 Drawing Sheet

METHOD AND APPARATUS FOR ANALYZING BLOOD

BACKGROUND OF THE INVENTION

This application is a continuation-in-part of co-pending application Ser. No. 307,227, filed Feb. 6, 1989 since abandoned, which is a continuation of application Ser. No. 110,972, filed Oct. 20, 1987, since abandoned.

The present invention pertains generally to blood collecting chambers. More particularly, the present invention pertains to chambers for collecting blood from a patient, analyzing the blood and returning the blood to the body without exposing the blood to the ambient air. The present invention is particularly, but not exclusively, useful for the continuous monitoring of arterial blood oxygen in neonates or adults.

DISCUSSION OF THE PRIOR ART

In numerous medical procedures, there is a recognized need to monitor the arterial oxygen status of critically ill infants and adults. Accordingly, several devices have been proposed which are intended to provide current, objective and clinically useful data for this purpose. Typically, these devices are non-invasive and provide for transcutaneous oxygen monitoring. Examples of such devices include the Oxymonitor TM marketed by Litton Medical Electronics, the tcomette portable transcutaneous oxygen monitor marketed by Novametrix Medical Systems Inc. and the TCM1 TC Oxygen Monitor marketed by Radiometer Copenhagen.

The transcutaneous monitoring of arterial oxygen status, as should be expected, has its difficulties. Most important of these difficulties is the potential for inaccurate measurements. For example, transcutaneous measurements rely on good perfusion (vasodilation) of cutaneous blood vessels. This requires heating of the patient's skin surface to arterialize the cutaneous blood vessels. This heating, however, necessitates the use of precisely calibrated equipment and careful monitoring of the equipment to avoid skin burns. In sum, transcutaneous procedures encounter many variables which must be reconciled to ensure accurate, reliable, and safe measurements. On the other hand, direct readings from arterial blood circumvents many of these variables.

Direct readings of arterial blood status, however, can also present difficulties. A main concern in such a procedure is the need for frequent measurements and the consequent need to repeatedly remove blood from the patient. This loss of blood can be critical. This is particularly so for neonates. In any event, there is the need to replace the withdrawn blood through a transfusion procedure. A transfusion, however, exposes the patient to other risks such as infection (e.g. hepatitis or AIDS) or transfusion reaction. These risks should be avoided if possible. Further, whenever blood is drawn from the patient, there is the possibility that the blood sample will be exposed to the ambient air which will introduce inaccuracies into the measurement of the blood's oxygen status.

The present invention recognizes that direct blood sampling can be accomplished for monitoring a patient's arterial oxygen status while using a system which allows replacement of the analyzed blood. Thus, there is no blood loss. Further, the present invention recognizes that a patient's arterial oxygen status can be measured without exposing the blood sample to the ambient air and that the sample can be infused back into the patient after the oxygen status of the sample has been measured.

Accordingly, it is an object of the present invention to provide an apparatus for measuring the arterial oxygen status of a patient which is accurate, reliable and current. Another object of the present invention is to provide an apparatus for making direct measurements of blood oxygen status without exposing the blood sample to the ambient air. Still another object of the present invention is to provide a blood sampling chamber which permits infusion of the blood sample back into the patient after the sample has been monitored. Yet another object of the present invention is to provide means which prevents unwanted contact of the patient's blood with others. Another object of the present invention is to provide a blood sampling chamber which is easy to use, which is cost effective and which can be easily manufactured.

SUMMARY OF THE INVENTION

The preferred embodiment of the apparatus for analyzing the blood of a patient comprises a conduit formed with a fluid passageway therethrough. This conduit is formed with an inlet, an outlet and a seating surface which defines an aperture therethrough, each of which is individually in fluid communication with the passageway. An adapter, which is threadably engageable with the conduit, holds a polypropylene membrane over the aperture between the seating surface of the conduit and the periphery of the adapter. The adapter is also engageable with the electrode of a blood gas analyzer to position the electrode against the side of the membrane opposite the passageway. Means are provided to connect the inlet of the conduit into fluid communication with an artery of the patient and a syringe is engageable with the outlet to draw blood into the passageway through the inlet. A valve, in fluid communication with a fluid source, can be provided in the fluid line between the patient and the conduit to alternatingly establish fluid communication between the patient and either the conduit or the fluid source.

The novel feature of this invention, as well as the invention itself, both as to its structure and its operation will be best understood from the accompanying drawings, taken in conjunction with the accompanying description, in which similar reference characters refer to similar parts, and in which:

DESCRIPTION OF THE PREFERRED EMBODIMENT

Figure 1:
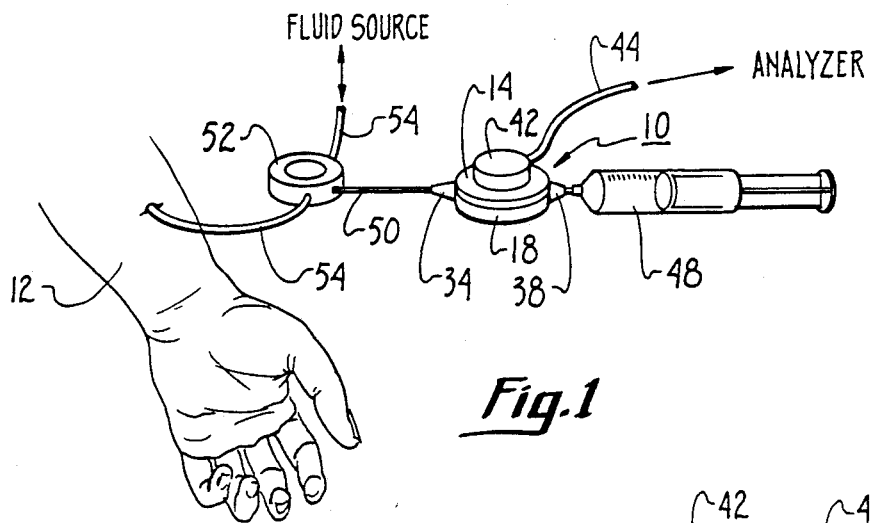
FIG. 1 is a perspective view of the blood collecting chamber of the present invention in its intended environment.
Figure 2:
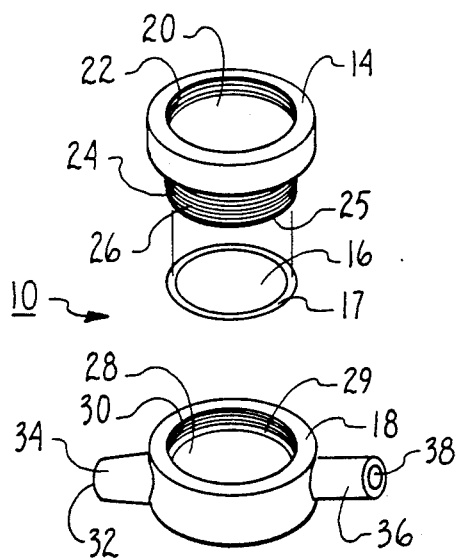
FIG. 2 is an exploded perspective view of the chamber.

Referring initially to FIG. 1, the blood collecting chamber of the present invention, generally designated 10, is shown in its intended environment operatively connected to a patient 12. More specifically, FIG. 2 shows that the chamber 10 comprises an adapter 14, a membrane 16 and a conduit 18. Adapter 14 is generally annular-shaped to form an opening 20 which is defined, at least in part, by a threaded surface 22. Adapter 14 is also formed with a skirt 24 having a periphery 25 and a threaded surface 26 as shown. For the purpose of the present invention, membrane 16 is preferably polypropylene and is manufactured in a manner well known in the relevant art. Any material, however, which is well known in the pertinent art that will permit detection of blood oxygen status therethrough by a gas blood analyzer may be used. Additionally, membrane 16 may be formed with a metallic reinforcing ring 17 which circumscribes membrane 16 to maintain the shape of membrane 16. Alternatively, ring 17 can be formed as a thickened ridge of the same material used for membrane 16. Further, ring 17 may be of any other suitable material which is chemically compatible with the fluids to be analyzed by the blood collecting chamber 10 of the present invention.

As best seen in FIG. 2, conduit 18 is formed with an aperture 28 having a periphery that is partly defined by a threaded surface 30. Conduit 18 is also formed with a nozzle 32 extending therefrom to define an inlet 34. Additionally, conduit 18 is formed with a connector 36 which defines an outlet 38. Finally, a portion of threaded surface 30 extends into and circumscribes aperture 28 to form a seating surface 29.

Figure 3:
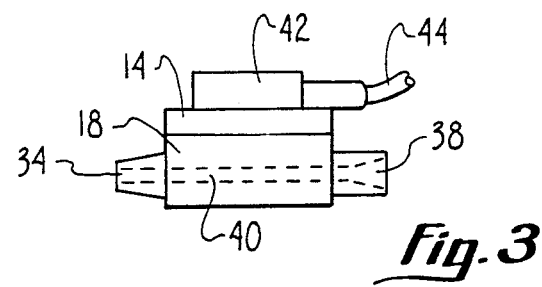
FIG. 3 is a side elevational view of the chamber connected to an electrode with portions shown in phantom for clarification.

Referring for the moment to FIG. 3, it will be seen that a passageway 40 is established in conduit 18 which is in fluid communication with both inlet 34 and outlet 38. Further, FIG. 2 shows that when chamber 10 is unassembled, aperture 28 also opens directly into passageway 40.

As will be best appreciated by reference to FIG. 2, chamber 10 can be assembled by attaching circular-shaped membrane 16 to periphery 25 of the skirt 24 of adapter 14 by any means well known in the art, such as by solvent bonding. The combination of adapter 14 and membrane 16 is then threadably engaged with conduit 18 by the interaction of threaded surface 26 with threaded surface 30. It will be understood by the skilled artisan, however, that any means well known in the art may be used to join adapter 14 to conduit 18. The threaded engagement disclosed here is but one means for providing a fluid tight engagement between adapter 14 and conduit 18. Alternatively, membrane 16 could be fixedly attached, such as by solvent bonding, to seating surface 29 of conduit 18. Further, it is to be understood that membrane 16 need not necessarily be bonded to periphery 25 of adapter 14 or seating surface 29 of conduit 18. Indeed, membrane 16 may be merely positioned in aperture 28 and removably held between periphery 25 of adapter 14 and seating surface 29 of conduit 18 by the interaction of these structures. In any event, when properly placed, membrane 16 defines part of passageway 40.

Figure 4:
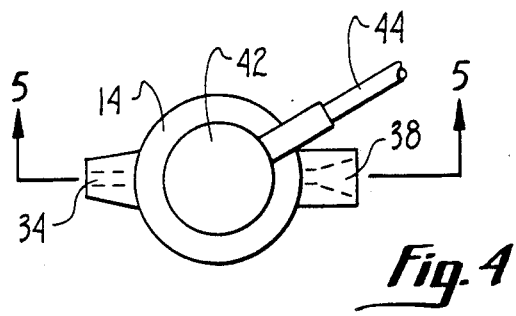
FIG. 4 is a top plan view of the chamber connected to an electrode with portions shown in phantom for clarification.
Figure 5:
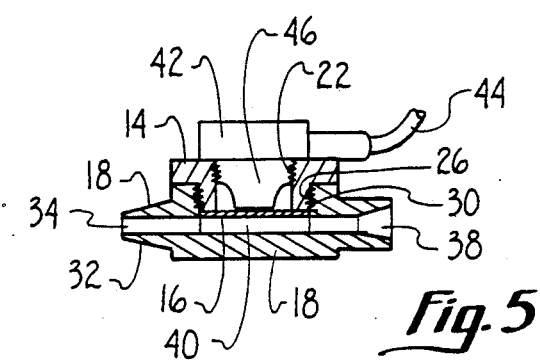
FIG. 5 is a side cross sectional view of the chamber connected to an electrode as seen along the line 5—5 in FIG. 4.

FIG. 3 shows that an electrode 42 of a blood gas analyzer (not shown) can be joined to adapter 14 of chamber 10. Specifically, electrode 42 can be threadably engaged with adapter 14 through its interaction with threaded surface 22, as shown in FIG. 5. Electrode 42, as shown in FIG. 3, is connected with a cable 44 which is electrically connected to the blood gas analyzer (not shown). As contemplated by the present invention, a gas blood analyzer such as the one marketed by Litton Medical Electronics under the trademark Oxymmitor TM may be used. Other analyzers, such as the TCM1 TC OXYGEN MONITOR marketed by Radiometer Copenhagen, may also be adapted for use with the present invention. By cross-referencing FIG. 3 and FIG. 4, it will be seen how an analyzer like those referenced above can be associated with chamber 10 of the present invention.

FIG. 5 best shows the interaction of electrode 42 with chamber 10. Specifically, in FIG. 5, it is seen that a probe 46 of electrode 42 extends into opening 20 of adapter 14 to make contact with membrane 16. This connection places electrode 42 in operative contact against the side of membrane 16 which is opposite passageway 40. Again, although FIG. 5 shows threaded connections between adapter 14 and respectively electrode 42 and conduit 18, any means well known in the pertinent art for connecting these structures may be used.

FIG. 1 shows chamber 10 operatively associated with other components necessary for operation of the present invention. Specifically, FIG. 1 shows a syringe 48 connected in fluid communication with outlet 38. Also shown is a tube 50 which is connected in fluid communication with inlet 34 to establish a fluid pathway between chamber 10 and a valve 52. Valve 52 is of any type well known in the pertinent art that can be used to establish a fluid pathway between patient 12 and either a fluid source (not shown) or chamber 10. An IV line 54 may be connected to valve 52, as shown in FIG. 1, for establishing the fluid pathway between patient 12 and a fluid source.

OPERATION

For the operation of the blood collecting chamber 10 of the present invention, an electrode 42 of a blood gas analyzer (not shown) is threadably joined with adapter 14 of chamber 10 substantially as shown in FIGS. 1, 3, 4 and 5. Then, membrane 16 may be placed onto seating surface 29 of conduit 18 and adapter 14 threaded into conduit 18 to hold membrane 16 between seating surface 29 and periphery 25 of adapter 14. This connection places probe 46 of electrode 42 into operative contact with the membrane 16. Inlet 34 of chamber 10 is then connected into fluid communication with an artery of patient 12 by any means known in the pertinent art. As disclosed above, valve 52 may be incorporated between chamber 10 and patient 12 to alternatively establish a fluid path between patient 12 and a fluid source (not shown).

With chamber 10 connected in fluid communication with patient 12, as disclosed, a partially flush-filled syringe 48 is engaged with outlet 38. With valve 52 configured to establish a fluid pathway from the patient 12 to chamber 10, syringe 48 is manipulated to draw blood from patient 12 through chamber 10 into syringe 48. This causes blood in passageway 40 to contact the side of membrane 16 opposite electrode 42 and establish a connection therebetween which will allow the blood gas analyzer to analyze the blood in passageway 40.

Once the analysis has been accomplished, syringe 48 can be manipulated to infuse the previously drawn blood back into patent 12. Valve 52 can then be configured to restablish fluid communication between patient 12 and the fluid source. Subsequently, membrane 16 may be replaced with a new, sterile membrane (not shown) by disengaging adapter 14 from conduit 18. Membrane 16 may then be removed from seating surface 29 of conduit 18 and the new membrane (not shown) placed onto seating surface 29. Adapter 14 is then threaded back into conduit 18 to hold membrane 16 in place, and the entire process repeated as necessary.

For the embodiments of chamber 10 wherein membrane 16 is fixedly attached to either periphery 25 of adapter 14 for seating surface 29 of conduit 18, adapter 14 or conduit 18, as appropriate, may be replaced after use with respectively a new adapter (not shown) or new conduit (not shown).

While the particular apparatus for analyzing the oxygen content of blood as herein shown and disclosed in detail is fully capable of obtaining the objects and providing the advantages herein before stated, it is to be understood that it is merely illustrative of the presently preferred embodiment of the invention and that no limitations are intended to the details of construction or design herein shown other than as defined in the appended claims.

I claim:

1. A blood analyzing device, which comprises:
   a blood gas analyzer;
   a conduit comprising a passageway constructed so as to collect and hold blood, said conduit being further formed with an inlet constructed so as to provide blood flow from a patient to said passageway, an outlet and a seating surface defining an aperture therethrough;
   an annular-shaped adapter comprising a periphery which defines an opening therethrough, said periphery comprising an outer surface threadably engaged with said conduit and having a threaded inner surface engaged with said analyzer;
   a replaceable membrane comprising a first side and a second side, said membrane being removably held between said periphery of said adapter and said seating surface of said conduit to removably cover said aperture with said first side being exposed to said passageway to define part of said passageway and to provide surface contact with the collected blood, said second side of said membrane exposed to contact said analyzer and establish an electrical contact therebetween to analyze the blood in said passageway; and
   means engaged with said conduit outlet constructed so as to draw blood from the patient into said passageway through said inlet to bring blood into contact with said first side of said membrane.

2. A blood analyzing device as recited in claim 1 wherein said membrane further comprises a reinforcing ring circumscribing said membrane.

3. A blood analyzing device as recited in claim 1, wherein said passageway is defined by, and continually passes through, said inlet and said outlet.

4. A blood analyzing device as recited in claim 1, wherein said seating surface of said conduit is formed on an inner surface of said conduit, said seating surface being positioned so as to abut said adapter.

5. A method for analyzing blood, which comprises:
   (a) engaging a syringe with a blood collecting chamber which comprises an annular shaped adapter defining a periphery, said periphery comprising a threaded inner surface and a threaded outer surface and forming an opening therethrough, a replaceable electrically conductive membrane to removably cover said opening; a conduit forming said chamber and comprising a fluid passageway therethrough, said conduit further comprising an inlet constructed so as to provide blood flow from a patient to said passageway, an outlet, and a seating surface defining an aperture therethrough, said conduit threadably engaged with the outer surface of said adapter removably holding said membrane between said periphery of said adapter and said seating surface of said conduit to define part of said chamber; and an electrode electrically connected to a blood gas analyzer, said analyzer having means threadably engaged with the inner surface of said adapter to hold said electrode against said membrane to establish electro-chemical contact with said membrane;
   (b) manipulating said syringe to draw blood into said passageway through said inlet; and
   (c) energizing said analyzer to analyze the blood in said passageway.

6. A method for analyzing blood as recited in claim 5 wherein said membrane further comprises a reinforcing ring circumscribing said membrane.

* * * * *